United States Patent
Shim

(10) Patent No.: US 11,612,677 B2
(45) Date of Patent: Mar. 28, 2023

(54) SCAFFOLD MATERIALS MANUFACTURED VIA BIO 3D PRINTING TECHNIQUE, AND PREPARATION METHOD OF THREE-DIMENSIONAL SCAFFOLDS USING THE MATERIALS

(71) Applicant: INCHEON UNIVERSITY INDUSTRY ACADEMIC COOPERATION FOUNDATION, Incheon (KR)

(72) Inventor: Min Suk Shim, Guri-si (KR)

(73) Assignee: INCHEON UNIVERSITY INDUSTRY ACADEMIC COOPERATION FOUNDATION, Incheon (KR)

( * ) Notice: Subject to any disclaimer, the term of this patent is extended or adjusted under 35 U.S.C. 154(b) by 1028 days.

(21) Appl. No.: 16/339,363

(22) PCT Filed: Aug. 24, 2017

(86) PCT No.: PCT/KR2017/009244
§ 371 (c)(1),
(2) Date: Apr. 4, 2019

(87) PCT Pub. No.: WO2018/070658
PCT Pub. Date: Apr. 19, 2018

(65) Prior Publication Data
US 2020/0038557 A1    Feb. 6, 2020

(30) Foreign Application Priority Data

Oct. 11, 2016 (KR) .................. 10-2016-0131120

(51) Int. Cl.
| | |
|---|---|
| A61L 27/00 | (2006.01) |
| A61L 27/56 | (2006.01) |
| B33Y 70/00 | (2020.01) |
| B29C 64/112 | (2017.01) |
| B29C 64/245 | (2017.01) |
| A61L 27/54 | (2006.01) |
| C08K 5/053 | (2006.01) |
| C08L 63/08 | (2006.01) |
| B33Y 10/00 | (2015.01) |
| B33Y 80/00 | (2015.01) |

(52) U.S. Cl.
CPC ............ *A61L 27/56* (2013.01); *A61L 27/54* (2013.01); *B29C 64/112* (2017.08); *B29C 64/245* (2017.08); *B33Y 70/00* (2014.12); *C08K 5/053* (2013.01); *C08L 63/08* (2013.01); *A61L 2300/414* (2013.01); *A61L 2400/18* (2013.01); *B33Y 10/00* (2014.12); *B33Y 80/00* (2014.12)

(58) Field of Classification Search
CPC ........... A61L 27/18; A61L 27/52; A61L 27/56
See application file for complete search history.

(56) References Cited

U.S. PATENT DOCUMENTS

2003/0120228 A1 * 6/2003 Koenig ............... A61L 15/46
                                                                 604/385.01
2011/0244054 A1   10/2011 Sigurjonsson et al.

FOREIGN PATENT DOCUMENTS

| KR | 10-2010-0128565 A | 12/2010 |
| KR | 10-2015-0121570 A | 10/2015 |
| KR | 10-2016-0095481 A | 8/2016 |
| KR | 10-2016-0096829 A | 8/2016 |

OTHER PUBLICATIONS

International Search Report for PCT/KR2017/009244 dated Nov. 30, 2017 from Korean Intellectual Property Office.

* cited by examiner

*Primary Examiner* — Jason-Dennis N Stewart
(74) *Attorney, Agent, or Firm* — Revolution IP, PLLC

(57) ABSTRACT

The present invention relates to a raw material for a bio-3D printing support and, more specifically, to a novel type bio-3D printing support material for tissue engineering, a method for manufacturing a three-dimensional support by using the same, and a 3D-printing three-dimensional support manufactured thereby, the raw material: being non-toxic and implementing excellent biocompatibility and cell adhesion since a raw material for a tissue engineering support (scaffold) produced by bio-3D printing technology, a specific fatty acid and a fatty alcohol (phase change material) derived from a natural source having a low melting point and a low molecular weight are used; and, in particular, allowing a phase change to easily occur at a temperature similar to body temperature such that a process is simplified and cells or growth factors can be mixed.

10 Claims, No Drawings

SCAFFOLD MATERIALS MANUFACTURED VIA BIO 3D PRINTING TECHNIQUE, AND PREPARATION METHOD OF THREE-DIMENSIONAL SCAFFOLDS USING THE MATERIALS

FIELD OF THE INVENTION

The present invention relates to a raw material for a bio-3D printing support and, more specifically, to a novel type bio-3D printing support material for tissue engineering, a method for manufacturing a three-dimensional support by using the same, and a 3D-printing three-dimensional support manufactured thereby, the raw material: being non-toxic and implementing excellent biocompatibility and cell adhesion since a raw material for a tissue engineering support (scaffold) produced by bio-3D printing technology, specific fatty acid and fatty alcohol (phase change material) derived from a natural source having a low melting point and a low molecular weight are used; and, in particular, allowing a phase change to easily occur at a temperature similar to body temperature such that a process is simplified and cells or growth factors can be mixed.

BACKGROUND OF THE INVENTION

Tissue engineering is a technology enabling maintenance of biological function, improvement and recovery by implanting biological substitutes into a body based on basic principles and technique of life science, medicine and engineering.

For example, the implementation of tissue engineering starts to collect required tissues from a patient and separate cells from the tissues. Additionally, the required amounts of the cells are cultured and proliferated and transplanted into a biodegradable support (e.g. Scaffold) with multiple pores. After the transplantation, the cells are cultured for a fixed period and the support is implanted into the patient. After the implantation, oxygen and nutrients for the cells are supplied from diffusion of body fluid until new blood vessels are created in a tissue or an organ. The cells are proliferated and thus form new tissues and organs when blood is provided by the new blood vessel. Further, the biodegradable polymer support is degraded and disappeared.

The requirements of material used for the support are as follows. A tissue cell should attach to the surface of the support and the support should have a mechanical strength as a support which enable the tissue cell to form a tissue with three dimensional structure. Further, the support should be biocompatible without toxicity where blood coagulation or inflammation does not occur after implantation. Moreover, the support should be biodegradable, which means that the support is completely decomposed and disappeared within a desired time when the implanted cells play a role as a new tissue.

3D bio-printing technology related to the production of a support for tissue engineering have been rapidly developed.

However, the raw materials used in the bio-3D printing technology for producing a three-dimensional support is limited to synthetic polymers and research for a new raw material hardly proceeds.

Specifically, most of the supports manufactured by the bio 3D printing technology are decomposable synthetic polymers approved by the FDA, namely, PLGA (Poly (lactic-co-glycolic acid)), PCL (Poly(caprolactone)), PLA (Poly (lactic acid)), PGA (Poly(glycolic acid)).

Synthetic polymers such as PLGA and PCL have more excellent properties and higher biocompatible than other synthetic polymers. However, the polymers can induce inflammation in a tissue, which is caused by acidic by-products made in degradation of the polymers.

Additionally, extrusion molding should be made by injecting liquid material in a cylinder when manufacturing a support based on 3D printing technology, and thus a process for melting solid polymers is required. The melting is made over 80° C. and thus it is difficult to mix growth factors or cells susceptible to temperature into the polymer support.

DETAILED DESCRIPTION OF THE INVENTION

Problems to be Solved

The present invention aims to solve the existing problems, and thus the technical goal of the present invention is to provide a raw material for a new type of a support used in bio 3D printing, which has properties of excellent cell-adhesion, biocompatibility (non-toxicity) and biodegradability. Additionally, phase change of the material arises easily in temperature similar to body temperature compared to existing synthetic polymers and thus can simplify a process for bio 3D printing as well as implement injection of cells and growth factors susceptible to temperature.

Solution

In order to solve the problem, the present invention provides a raw material for a support used in bio 3D printing, comprising one or more of fatty acid and fatty alcohol, the fatty acid and the fatty alcohol are phase change materials (e.g., lauric acid (Dodecanoic acid) and 1-tetra-decanol) which are solid state at room temperature and melting points of the fatty acid and the fatty alcohol are 35~45° C., and which is used for producing a support (scaffold) using bio 3D printing technology.

Further, in another aspect, the present invention provides a method for preparing a three-dimensional support using bio 3D printing technology, comprising S1) manufacturing a solution by melting the raw material at the range from room temperature to 45° C.; S2) injecting the solution into a receiving part; and S3) discharging the solution through a nozzle capable of moving in three dimensions by applying pressure to the receiving part, and stiffening the solution.

In another aspect, the present invention provides a three-dimensional support manufactured by the method, which is based on fatty acid and fatty alcohol.

Benefits of the Invention

A certain fatty acid (e.g., lauric acid) and fatty alcohol (e.g., 1-tetra-decanol) proposed by the present invention are a material obtained from natural materials and thus are non-toxic. Additionally, the fatty acid and the fatty alcohol have an excellent biocompatibility and high biodegradability.

Further, melting points of the fatty acid and the fatty alcohol are around 35~40° C. and thus the phase change arises easily in temperature similar to body temperature. As a result, the fatty acid and the fatty alcohol liquefies and promotes simplification of a process, and enables temperature-susceptible factors such as cells and growth factors to be injected into a support.

Additionally, cell adhesion of the fatty acid and the fatty alcohol is remarkable due to hydrophobic property and thus cells are attached easily to a support, and the price is very affordable.

Consequently, the fatty acid and fatty alcohol of the present invention can be used suitable for a raw material of a support used in bio 3D printing.

DETAILED DESCRIPTION FOR IMPLEMENTING THE INVENTION

Hereinafter, the present invention will be described in details.

A raw material for a support used in bio 3D printing in the present invention comprises one or more of fatty acid and fatty alcohol, wherein the fatty acid and the fatty alcohol are phase change materials which are solid state at room temperature and melting points of the fatty acid and the fatty alcohol are 35~45° C., and which is used for producing a support (scaffold) using bio 3D printing technology.

The fatty acid and the fatty alcohol are low molecular-weight materials which are solid state at room temperature and liquefy easily at low temperature around body temperature compared to existing synthetic polymers. Therefore, the fatty acid and the fatty alcohol can be used simply and are non-toxic as natural materials. As a result, biocompatibility of the fatty acid and the fatty alcohol is outstanding.

In a preferred embodiment, the fatty acid can be lauric acid (Dodecanoic acid), and the fatty alcohol can be 1-tetra-decanol.

The lauric acid is a normal 1 basic saturated fatty acid having twelve carbons ($C_{12}H_{24}O_2$; Molecular Weight 200) and exist in status of glyceride in coconut oil, palm oil or pulp oil of laurel. The lauric acid has a state of white powder at room temperature and the melting point of lauric acid is 43.5~44° C.

The 1-tetra-decanol is normal saturated fatty alcohol ($C_{14}H_{30}O$; Molecular Weight 214) having fourteen carbons, and exist in status of fatty acid ester in fruit oil of nutmeg, fruit fat of lady palm, milk fat and sperm oil. The 1-tetra-decanol has a state of white crystalline, and the melting point of the 1-tetra-decanol is 37.6~38° C.

Additionally, the fatty acid and the fatty alcohol are non-toxic and the price is affordable as well as the purchase is easy.

One of the fatty acid and the fatty alcohol or the mixture thereof can be used in the present invention.

In the mixture, the fatty acid and the fatty alcohol can be mixed in weight ratio of 1:9~9:1 but not limited thereto.

A synthetic polymer used normally in conventional bio 3D printing can be combined with the fatty acid and/or the fatty alcohol for the purpose of reinforcing physical properties such as mechanical strength.

In an embodiment, the synthetic polymer can be one or more selected from a group consisting of PLGA (Poly(lactic-co-glycolic acid)), PCL (Poly(caprolactone)), PLA (Poly(lactic acid)) and PGA (Poly(glycolic acid)). Further, another synthetic polymer such as PU and PEG; or proteins such as collagen, albumin and gelatin can be used.

When mixing the synthetic polymer with the fatty acid and/or the fatty alcohol, the mixing ratio by weight of the fatty acid and/or the fatty alcohol: the synthetic polymer can be 8:2~9:1. The property might not be reinforced when too small amounts of the synthetic polymer not within the range are combined, and inflammation in a tissue might arise or high temperature might be required for melting when too much amounts of the synthetic polymer not within the range are combined, which hinder the achievement of the purpose of the present invention.

Particularly, a raw material in the present invention further comprises one or more selected from a group consisting of a cell, a growth factor and a drug, preferably, both of a certain cell and a growth factor enabling the cell to grow.

A form of a preferable support known so far is that a cell becoming to a tissue and growth factor enabling the cell to grow exist together in a three-dimensional support. In other words, when using the fatty acid and the fatty alcohol of the present invention, a three-dimensional support with high biocompatibility can be manufactured by comprising both of a cell and a growth factor at low temperature through bio 3D printing technology. Therefore, the support is non-toxic when implanting into a body and the efficiency of tissue regeneration can be improved significantly.

A method for preparing a three-dimensional support through bio 3D printing based on the raw material of the present invention is not limited and a normal process and a normal bio 3D printing technology in the art such as 3D Plotting can be used for preparing a three-dimensional support.

For example, a support for bio 3D support printing in the present invention can be manufactured by a bio 3D printing technology, comprising:

S1) manufacturing a solution by melting a raw material mentioned above at the range from room temperature to 45° C.; S2) injecting the solution into a receiving part; and S3) discharging the solution through a nozzle capable of moving in three dimensions by applying pressure to the receiving part, and stiffening the solution.

The step S1) is to liquefy a raw material consisting of fatty acid and/or fatty alcohol by heating the raw material at moderate temperature which is beyond melting point of it.

In other words, phase change of the raw material in the present invention arises easily at temperature similar to body temperature, and thus mixing susceptible factors such as a cell, a growth factor and a drug can be incorporated in a process of bio 3D printing.

The step S2) is to inject the raw material produced in the step S1) into a receiving part (e.g., cylinder) connected to a nozzle.

The step S3) is to form a three-dimensional shaped scaffold by pushing the raw material injected from the receiving part by air pressure through the nozzle.

More specifically, a cylinder head is placed for moving freely to XYZ direction according to adjustment of a moving part, and the melted raw material is discharged through the nozzle. Then, the raw material is stiffened soon after contacting to a surface of the formed scaffold or a bottom and thereby a three-dimensional shape can be manufactured. At this time, a moving path of the moving part can be pre-programmed and a scaffold with complicated shape can be manufactured in the way.

In the step, a skilled person in the art can manipulate pressure on the receiving part (e.g., 10~300 kPa), a diameter of a nozzle output (e.g., 0.1~0.5 mm) and moving rate of the nozzle (e.g., 50~400 mm/min), considering constant discharge of the raw material, accuracy of the three-dimensional shape, good stiffness and productivity.

Additionally, in the method for preparing a three-dimensional support of the present invention, it is preferable that sterilization of the manufactured three-dimensional support is performed further for the purpose of tissue engineering. The sterilization method is not limited and a normal sterilization method in the art can be used.

Hereinafter, the present invention will be described in details based on examples. However, the examples are only for helping understand the present invention and the present invention is not limited thereto.

Example 1

After earning lauric acid as raw material, it was melted at 44° C.

The melted raw material was injected into a cylinder equipped with a movable nozzle in three dimensions.

Pressure (200 kPa) was applied to the cylinder and then the melted raw material was discharged through the nozzle (diameter: 0.3 mm) moving (200 mm/min) along a programmed path in three dimensions. Moreover, a three-dimensional support with laminated structure was formed by stiffening the raw material and then sterilized.

Example 2

Procedure was the same as Example 1 except using 1-tetra-decanol as raw material and melting the raw material at 38° C.

Example 3

Procedure was the same as Example 1 except using a compound as raw material that lauric acid and 1-tetra-decanol were mixed with the same weight ratio.

Example 4

Procedure was the same as Example 1 except mixing lauric acid with haematopoietic stem cell counted to the predetermined numbers and growth factor (SCF), and then melting the raw material.

INDUSTRIAL UTILITY

The present invention provides a non-toxic new raw material replacing synthetic polymers (e.g., PLGA and PCL) used as a support for conventional bio 3D printing.

The fatty acid and/or the fatty alcohol according to the present invention is a material whose phase change arise easily and thus a process for bio 3D printing can be simplified and the cost can be saved.

Additionally, The fatty acid and/or the fatty alcohol according to the present invention is affordable but can be a raw material for a support based for bio 3D printing, which is a valuable product. Consequently, much applications and marketability can be anticipated in tissue engineering.

What is claimed is:

1. A raw material for a support used in bio 3D printing, comprising both a fatty acid and fatty alcohol,
   wherein the fatty acid and the fatty alcohol are phase change materials which are solid state at room temperature and melting points of the fatty acid and the fatty alcohol are 35~45° C.,
   wherein the raw material is used for manufacturing a three-dimensional support(Scaffold) using bio 3D printing technology, and
   wherein the raw material comprises the fatty acid and the fatty alcohol, and the fatty acid is mixed with the fatty alcohol in weight ratio of 1:9~9:1.

2. The raw material of the claim 1, wherein the raw material further comprises a synthetic polymer.

3. The raw material of the claim 2, wherein the synthetic polymer is one or more selected from a group consisting of PLGA(Poly(lactic-co-glycolic acid)), PCL(Poly(caprolactone)), PLA(Poly(lactic acid)) and PGA(Poly(glycolic acid)).

4. The raw material of the claim 3, wherein one or both of the fatty acid and the fatty alcohol are mixed with the synthetic polymer in weight ratio of 8:2~9:1.

5. The raw material of the claim 1, wherein the raw material further comprises one or more selected from a group consisting of a cell, a growth factor and a drug.

6. The raw material of the claim 5, wherein the raw material comprises both of the cell and the growth factor enabling the cell to grow.

7. A method for preparing a three-dimensional support using bio 3D printing technology, comprising:
   S1) manufacturing a solution by melting a raw material according to claim 1 at the range from room temperature to 45° C.;
   S2) injecting the solution into a receiving part; and
   S3) discharging the solution through a nozzle capable of moving in three dimensions by applying pressure to the receiving part, and stiffening the solution.

8. The method of the claim 7, wherein the melting in the S1) is made by mixing one or both of the fatty acid and the fatty alcohol with one or more selected from a group consisting of a cell, a growth factor and a drug.

9. The method of the claim 7, wherein the method further comprises a step of sterilizing the manufactured 3D support.

10. A 3D support based on fatty acid and fatty alcohol, manufactured by a method according to claim 7.

* * * * *